United States Patent [19]

Straub et al.

[11] 4,254,239

[45] Mar. 3, 1981

[54] BIODEGRADABLE VINYLPYRROLIDONE POLYMERS, THEIR MANUFACTURE AND USE

[75] Inventors: Ferdinand Straub, Hockenheim; Hans-Uwe Schenck, Wachenheim; Siegfried Lang, Ludwigshafen; Egon Brode, Frankenthal, all of Fed. Rep. of Germany

[73] Assignee: BASF Aktiengesellschaft, Fed. Rep. of Germany

[21] Appl. No.: 973,798

[22] Filed: Dec. 28, 1978

[30] Foreign Application Priority Data

Dec. 31, 1977 [DE] Fed. Rep. of Germany ....... 2759150

[51] Int. Cl.³ .............................................. A61K 31/79
[52] U.S. Cl. ...................................... 525/123; 424/80;
525/361; 525/374; 525/386; 525/452; 525/453;
526/358; 525/336

[58] Field of Search ................... 424/80; 526/49, 358;
525/336, 359, 377, 374, 361, 386, 452, 453

[56] References Cited

U.S. PATENT DOCUMENTS

| | | | |
|---|---|---|---|
| 3,216,983 | 11/1965 | Shelanski et al. | 260/88.3 |
| 3,931,111 | 1/1976 | Kopecek et al. | 526/49 |
| 4,053,696 | 10/1977 | Hirrle et al. | 424/80 |

*Primary Examiner*—William F. Hamrock
*Attorney, Agent, or Firm*—Keil & Witherspoon

[57] ABSTRACT

High molecular weight products based on N-vinylpyrrolidone, in which blocks of vinylpyrrolidone polymers or vinylpyrrolidone copolymers are linked by connecting units carrying ester, amide, urethane or urea groups, as a result of which these high molecular weight products are biodegradable and may be used as plasma substitutes, and the plasma substitutes thus obtained.

6 Claims, No Drawings

BIODEGRADABLE VINYLPYRROLIDONE POLYMERS, THEIR MANUFACTURE AND USE

For first aid in cases of physiological shock, it is frequently necessary to use plasma substitutes, since blood stocks are in most cases not immediately available. Furthermore, it is necessary to be able to replace plasma without taking any risks as to compatibility (for example in respect of blood group and Rhesus factor). Pure salt solutions (physiological sodium chloride solution or Ringer's solution) are unsuitable for the treatment of shock, because their residence time in the vascular system is insufficient, and because they lack colloidal osmotic pressure (frequently referred to as oncotic pressure).

Polyvinylpyrrolidone solutions are already used extensively as plasma substitute. Because of their similarity to peptides, polyvinylpyrrolidones exhibit good compatibility and, provided they are of the appropriate medium molecular weight, their colloidal osmotic pressure resembles that of blood plasma. If their molecular weight is too high, however, they are not completely excreted and instead deposit in the reticuloendothelium. If on the other hand a polymer comprising only molecules of low molecular weight—to ensure good excretion via the kidneys—is used as the plasma substitute, the colloidal osmotic pressure, and hence the effectiveness of the substitute, is low. Polyvinylpyrrolidone is a very inert polymer since it is produced by free radical bipolymerization and hence its polymer chain consists of —C—C— bonds. Accordingly, the —C—C— bonds are not attacked by the body enzymes (from the blood and liver) and hence the polymers are not degraded.

German Pat. No. 1,041,052 describes a process for the preparation of polypeptide-like compounds from physiologically active compounds. According to this process, active ingredients are coupled to a vinylpyrrolidone/acrylic acid copolymer via peptide bridges and are after some time in vivo split off again by the enzymes. The manufacture of biodegradable polyvinylpyrrolidone by linking polyvinylpyrrolidone blocks by means of peptide units or analogously by means of sugar units is expensive and labor-intensive.

We have found that vinylpyrrolidone polymers and copolymers can be biodegraded if the polymer chain contains one or more

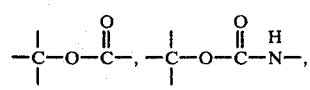

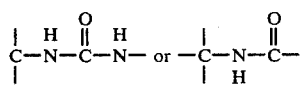

connecting units. In general, these are vinylpyrrolidone polymers wherein from 2 to 50 vinylpyrrolidone polymer or copolymer blocks having a degree of polymerization of from 2 to 1,000 are linked by connecting units containing ester, amide, urea or urethane groups, and which have average total molecular weights of from 1,000 to 1,000,000. The structure of such a vinylpyrrolidone polymer can conform to that of a block polymer

where A is a vinylpyrrolidone polymer block having a degree of polymerization of from 2 to 1,000, B is a connecting unit containing ester, amide, urea or urethane groups and n is from 0 to 50.

The number (n) of the blocks of vinylpyrrolidone polymer (A) and connecting units (B) containing ester, amide, urea or urethane groups depends on the one hand on the molecular weight of the vinylpyrrolidone polymer (A) and on the other hand on the desired molecular weight of the block polymer. If the mean molecular weight of the vinylpyrrolidone polymer A is low (for example from 500 to 5,000) and a high molecular weight of the block polymer (for example from 50,000 to 100,000) is desired, n must be high. Preferably, n is from 1 to 20. The proportion by weight of B in the block polymer (B-A) may be for instance from 1 to 50%, and if the molecular weight of B is high and that of A is relatively low, the proportion by weight of B may even exceed 50%.

The invention also relates to a process whereby low molecular weight vinylpyrrolidone polymers are converted to the above polymers, which have good colloidal osmotic properties and in vivo are degraded after some time and completely excreted through the kidneys.

To manufacture the said polymers, low molecular weight vinylpyrrolidone polymers with functional end groups are used as the starting materials and are linked by polycondensation or polyaddition reactions to give higher molecular weight polymers. Preferably, a bifunctional polymer, which can be manufactured by conventional methods, is used. Vinylpyrrolidone polymers with 2 functional end groups are obtained, for example, from vinylpyrrolidone by starting the polymerization with an initiator carrying functional groups, and adding a regulator which also transfers functional groups. For example, this can be done by polymerizing vinylpyrrolidone in aqueous solution with hydrogen peroxide, or by polymerizing vinylpyrrolidone by the method described in German Laid-Open Application DOS No. 2,514,127. If, for example, amines, eg. butylamine or toluidine, are used as regulators and azo-bis-isobutyroamidine as the initiator, a polyvinylpyrrolidone with amino end groups is obtained. The resulting vinylpyrrolidone homopolymers have long been employed as pharmaceutical auxiliaries and hence no longer require toxicological testing. However, it can be of advantage to employ copolymers of vinylpyrrolidone with other monomers because this allows the number of functional groups to be varied as desired. Examples of monomers copolymerizable with vinylpyrrolidone are acrylic acid, methacrylic acid, acrylamide, methacrylamide, allyl alcohol, hydroxyethyl acrylate, hydroxypropyl acrylate, butanediol monoacrylate and N-hydroxypropylacrylamide.

A further possible method of obtaining polyvinylpyrrolidone having OH end groups is to treat polyvinylpyrrolidone, obtained by free radical polymerization of N-vinylpyrrolid-2-one in the presence of hydrogen peroxide as the free radical initiator, with from 0.1 to 10, preferably from 0.5 to 5, % by weight—based on the polymer—of a complex hydride. Hydrides used are in particular water-soluble hydrides, for example sodium boranate and lithium boranate, but the reaction can also be carried out with others, for example $NaBH(OCH_3)_3$, $NaAlH_4$, $LiAlH_4$, $NaAlH_2(OCH_2OCH_3)_2$ or $LiAlH[(OC(CH_3)_3]$. The highly reactive complex hydrides are only employed in such amounts that the lactam group of the polyvinylpyrrolidone is not attacked.

The reaction with the complex hydrides is, where possible, carried out in water; this is feasible with lithium boranate and sodium boranate. In the case of the others, it is advantageous to use solvents, for example lower alcohols, eg. methanol, ethanol, iso-propanol, n-propanol, n-butanol or tert.-butanol, ethers, eg. dioxane or tetrahydrofuran, or aromatics, eg. benzene, toluene or xylene. The reaction is carried out at from 1° to 150° C., preferably from 15° to 80° C., depending on the boiling point of the solvent. If the reaction is carried out in an aqueous or alcoholic solvent, the pH is in general brought to about 7 before the reaction. The reaction time varies from 0.5 to 24 hours, preferably from 2 to 8 hours. If the polyvinylpyrrolidone contains carboxyl groups, it can be advantageous to esterify these by conventional methods before the reaction with a hydride.

A very useful method of removing impurities which might be present in the polymer has proved to be a treatment of the polymer solution with an ion exchanger. Examples of suitable ion exchangers are those based on polystyrene and possessing sulfo, carboxyl or quaternary ammonium groups, or those based on acid or basic silicates. Specific examples are the commercial products marketed under the trademarks AMBERLITE (Rohm & Haas Comp.) and LEWATIT (Bayer AG).

It is particularly preferred to purify the products after the reaction with the complex hydrides, since impurities formed during this reaction are thereby also removed. Polymers additionally treated in this way exhibit substantially higher reactivity in the polycondensation or polyaddition reaction than do the unpurified polymers.

Advantageous functional groups are hydroxyl or amino. The functional groups can also be introduced by copolymerizing the vinylpyrrolidone with comonomers carrying functional groups. Examples of such comonomers are mentioned above. The functional groups are advantageously selected in accordance with the connecting unit which it is desired to introduce into the molecule. For ester or urethane connecting units, a polymer with hydroxyl end groups is preferred, whilst polymers with amino end groups are preferred for amide or urea connecting units.

The molecular weight or degree of polymerization of the polymer is selected so that after in vivo degradation of the block polymers of the invention, the constituent polymer can be efficiently excreted through the kidneys. Hence, the degree of polymerization is from 2 to 1,000 and preferably from 10 to 300.

To form the units B, ie. the connecting units, containing ester, amide, urea or urethane groups, in the block polymers according to the invention, it is preferred to use bifunctional carboxylic acid derivatives or isocyanates, to ensure efficient linking. The number of splittable bonds, and the type of bond, can be decided by selection of the carboxylic acid derivatives or isocyanates. Hence, it is possible to predetermine the rate of enzymatic degradation. Examples of reactants used to produce the connecting units are the dicarboxylic acid halides e.g. phosgene, oxalyl chloride, malonic acid dichloride, succinic acid dichloride, glutaric acid dichloride, adipic acid dichloride, sebacic acid dichloride, phthalic acid dichloride and terephthalic acid dichloride, and diisocyanates, eg. toluylene diisocyanate, hexamethylene diisocyanate, methylene-biscyclohexylene diisocyanate and bis-(3-methyl-4-isocyanatocyclohexyl)-methane.

As is shown by the comments made in connection with the polymer blocks A and the connecting units B by which they are linked, ester connecting units are obtained on reacting polymers carrying hydroxyl groups with dicarboxylic acid derivatives, amide connecting units are obtained by reacting polymers carrying amino groups with dicarboxylic acid derivatives, urethane connecting units are obtained by reacting polymers carrying hydroxyl groups with diisocyanates and urea connecting units are obtained by reacting polymers carrying amino groups with diisocyanates.

Accordingly, the connecting units B each comprise two ester, amide, urethane or urea groups, linked by, for example, a direct bond (when using oxalyl chloride) or a methylene group (when using malonic acid dichloride). If phosgene is used, —A—B—A—B is —A—OCOO—A—OCOO—, ie. each B only contains one ester carbonyl group.

In general, the connecting units B may be derived, for example, from aliphatic dicarboxylic acids or diisocyanates in which the carboxyl groups are linked by a chain of from 0 to 10 carbon atoms or the two isocyanate groups are linked by a chain of from 1 to 10 carbon atoms.

The linking of the blocks A by the units B, ie. the polycondensation or polyaddition of the bifunctional vinylpyrrolidone polymer with the bifunctional carboxylic acid derivative or isocyanate is preferably carried out in solution. The solution should preferably be anhydrous so that the acid derivatives or isocyanates used for the linking reaction do not form any undesirable by-products. Suitable solvents are those which readily dissolve vinylpyrrolidone polymers and do not themselves undergo any reactions with the carboxylic acid derivatives or the isocyanates. Aprotic solvents, eg. N-methylpyrrolidone, dimethylsulfoxide, dimethylformamide, toluene and chlorohydrocarbons, are preferred.

To carry out the reaction, component A and the component required to form the connecting unit B may be mixed, or one component may be metered into a solution of the other.

After the reaction, the solvent can be removed by distillation or steam distillation, or by precipitating the block polymer.

The block polymers of the present invention exhibit good colloidal osmotic effects and are biodegradable, and the low molecular weight compounds resulting from such degradation are easily excreted through the kidneys. Their toleration is as good as that of the corresponding vinylpyrrolidone polymers without connecting units. They are therefore very suitable for use as pharmaceutical auxiliaries and as plasma expanders. The time required for their degradation by body enzymes is from several hours to several days. These properties are very surprising since synthetic polyesters, polyurethanes and polyamides, used as implants, will remain in the body for years without undergoing substantial degradation.

The Examples which follow illustrate the present invention without implying a limitation. The stated K values were measured by the method of H. Fikentscher, Cellulosechemie 13 (1932), 58–64 and 71–74. The molecular weight was calculated from the K value using the equation $M_w = 1.9 \times (K \text{ value})^3$.

EXAMPLES (1a) 100 g of polyvinylpyrrolidone of K value 14, prepared by polymerizing vinylpyrrolidone in aqueous solution with hydrogen peroxide as the initiator, and removing the pyrrolidone, are dissolved in 300 ml of chloroform; water is then removed by circulatory distillation. The solution is allowed to cool and when it is at room temperature, 12 ml of oxalyl chloride are added slowly. The solution becomes distinctly viscous and turns pale brown. It is stirred for 4 hours at room temperature and then neutralized with sodium bicarbonate, and the polymer is precipitated by dripping the reaction mixture into 2 liters of ether. The polymer has a K value of 17.6 (measured on a 5% strength solution in water), corresponding to a calculated molecular weight of 10,358.

Pyrrolidone can be removed from the starting polymer by, for example, purifying the solution over 2 kg of Lewatit S 100, after which the solution is freeze-dried and the residue is dissolved in 300 ml of chloroform.

(1b) 3 g of the polymer obtained as described in (1a) in 100 ml of deionized water and 100 ml of blood plasma are incubated for 16 hours at 37° and pH 7.2. The mixture is then freeze-dried, the powder is suspended in methylene chloride/methanol, the suspension is filtered and the solution obtained is precipitated in 200 ml of ether. A polymer having a K value of 14.2 is obtained.

(2a) 100 g of polyvinylpyrrolidone of K value 12, prepared by polymerization as described in German Laid-Open Application DOS No. 2,514,127, are dissolved in 300 ml of toluene; water is removed by circulatory distillation. The solution is allowed to cool and 9 ml of hexamethylene diisocyanate are then added. The mixture is left to stand overnight, a small amount of ethanol is then added and the organic solvent is removed by steam distillation. The resulting aqueous solution is slightly turbid. The K value of the polymer is 17.7.

(2b) The solution obtained as described in (2a) is incubated as described in (1b). A polymer having a K value of 12 is obtained.

(3a) 100 g of a copolymer of vinylpyrrolidone with 2-hydroxypropyl acrylate (95:5), having a K value of 18.1, are dissolved in 300 ml of dichloroethane. 9 ml of adipic acid dichloride are slowly added dropwise to the solution at room temperature and the mixture is left to stand overnight. Advantageously, it is then neutralized with sodium bicarbonate. Thereafter the polymer is precipitated by dripping the reaction mixture into 2 liters of ether. The powder has a K value of 24.3, corresponding to a calculated molecular weight of 27,262.

(3b) The polymer obtained as described in (3a) is incubated as described in (1b). After the incubation, the polymer has a K value of 19.3.

(4a) 100 g of polyvinylpyrrolidone of K value 14.3, prepared as described in German Laid-Open Application DOS No. 2,514,217, in ethanol as the solvent, are dissolved in 300 ml of methylene chloride; water is removed by circulatory distillation. The solution is cooled and 12 ml of succinic acid dichloride are added. The mixture is left to stand overnight and the polymer is precipitated by pouring into 2 liters of ether. The polymer is dissolved in 200 ml of water and neutralized with sodium bicarbonate; it has a K value of 16.2, corresponding to a calculated molecular weight of 8,078.

(4b) The solution obtained as described in (4a) is incubated as described in (1b). A polymer of K value 14.8 is obtained.

(5a) 100 g of a copolymer of vinylpyrrolidone and 2-hydroxypropyl acrylate (95:5), with a K value of 14.4, are dissolved in 300 g of chloroform and water is removed by circulatory distillation. After the mixture has cooled, 12 g of sebacic acid dichloride are added and the batch is left to stand overnight. It is then neutralized with sodium bicarbonate and the polymer is precipitated by dripping the solution into 2 liters of ether. The polymer has a K value of 17.1 (measured on a 5% strength solution in water), corresponding to a calculated molecular weight of 9,500.

(5b) The product (5a) is incubated as described in (1b). After incubation, the polymer has a K value of 16.7.

(6a) 100 g of a copolymer of vinylpyrrolidone and 2-hydroxypropyl acrylate (92.5:7.5), having a K value of 13.5, are dissolved in 300 g of dimethylformamide. 100 g of dimethylformamide are distilled off under reduced pressure. After the mixture has cooled, 12 g of toluylene diisocyanate are added and the batch is stirred for 4 hours. The polymer is precipitated by pouring into 2 liters of ether, and has a K value of 21.3 (measured on a 5% strength solution in water), corresponding to a calculated molecular weight of 18,360.

(6b) Product (6a) is incubated for six days as described in (1b). After the incubation, the product has a K value of 16.1.

(7a) 100 g of polyvinylpyrrolidone of K value 17, prepared by polymerizing vinylpyrrolidone in aqueous solution with hydrogen peroxide as the initiator, are treated, in aqueous solution, with 2 g of NaBH$_4$, and the mixture is stirred whilst it is frothing. The solution is then purified over 2 kg of Lewatit S 100 and Lewatit M 500. The freeze-dried polymer is dissolved in 300 g of dimethylformamide. 100 g of dimethylformamide are distilled off under reduced pressure. The solution is allowed to cool and 12 g of hexamethylene diisocyanate are added. The mixture is left to stand overnight and the polymer is precipitated by pouring into 2 liters of ether. The polymer has a K value of 27.9 (measured on a 5% strength solution in water), corresponding to a calculated molecular weight of 41,263.

(7b) The product from (7a) is incubated for six days as described in (1b). After the incubation, it has a K value of 24.6.

(8a) 100 g of polyvinylpyrrolidone of K value 17, prepared by polymerizing vinylpyrrolidone with hydrogen peroxide as the initiator, are treated, in aqueous solution, with 2 g of NaBH$_4$, and the mixture is stirred whilst it is frothing. The solution is then purified over 2 kg of Lewatit S 100 and Lewatit M 500. The freeze-dried polymer is dissolved in 300 g of chloroform. Water is removed by circulatory distillation, the mixture is allowed to cool, and 12 g of adipic acid dichloride are added. The batch is stirred for 4 hours and the polymer is precipitated by pouring into 2 liters of ether, and is dissolved in 200 g of water. After neutralizing with NaHCO$_3$, the polymer has a K value of 23.4, corresponding to a calculated molecular weight of 24,344.

(8b) The product of (8a) is incubated as described in (1b). After the incubation, it has a K value of 19.1.

COMPARATIVE EXAMPLE 1

A polyvinylpyrrolidone of K value 14, prepared by polymerizing in water by means of hydrogen peroxide, was incubated as described in (1b). After the incubation, the K value was still 14.

COMPARATIVE EXAMPLE 2

A polyvinylpyrrolidone of K value 12, prepared by polymerization as described in German Laid-Open Application DOS No. 2,514,127, was incubated as described in (1b). After incubation, the product had a K value of 12.4.

COMPARATIVE EXAMPLE 3

A copolymer of vinylpyrrolidone and 2-hydroxypropyl acrylate (95:5), having a K value of 18.1, was incubated as described in (1b). After the incubation, the polymer still had a K value of 18.1.

COMPARATIVE EXAMPLE 4

A polyvinylpyrrolidone of K value 14.3, prepared by polymerization as described in German Laid-Open Application DOS No. 2,514,127, was incubated as described in (1b). After incubation, the product had a K value of 14.4.

COMPARATIVE EXAMPLE 5

A polyvinylpyrrolidone of K value 17, prepared by polymerizing in water by means of hydrogen peroxide, reaction with $NaBH_4$ and purification over an ion exchanger, was incubated as described in (1b). After incubation, the polymer had a K value of 17.0.

To prepare plasma substitutes, the conventional methods for preparing pyrogen-free fluids can be employed, and physiological sodium chloride solution or Ringer's solution can also be admixed.

The following data, for example, can serve as guidelines for formulating plasma substitutes:

(a)
  biologically degradable polymer: 4.0 g
  electrolyte solution: ad 100 ml
  Composition of the electrolyte solution: 0.7 g of NaCl, 0.042 g of KCl, 0.05 g of $CaCl_2$, 0.0005 g of $MgCl_2$, 0.025 g of $NaHCO_3$, water (purified for injection) ad 100 ml.
  To prepare the plasma substitute, 4 g of the polymer are dissolved in the electrolyte solution, whilst stirring. The solution is passed through a filter to remove suspended particles, and is sterilized for 20 minutes at 120° C.; alternatively (b)
  biologically degradable polymer: 4.0 g
  physiological sodium chloride solution: ad 100 ml
  The solution obtained is filtered and then sterilized for 20 minutes at 120° C.

The addition of electrolyte solutions or salt solutions is advisable if it is desired to regulate or modify the osmotic pressure of the plasma substitute.

We claim:

1. A biodegradable vinylpyrrolidone polymer, usable as a blood plasma substitute, of the formula $$A-[B-A]_n-B-A$$

where A is a vinylpyrrolidone polymer or copolymer block having a degree of polymerization of from 2 to 1,000, B is a short-chain connecting unit containing ester, amide, urea or urethane groups which groups are formed by
  (a) hydroxyl groups in A and carboxylic acid groups in B resulting in ester groups,
  (b) amino groups in A and carboxylic acid groups in B resulting in amide groups,
  (c) amino groups in A and isocyanate groups in B resulting in urea groups,
  (d) hydroxyl groups in A and isocyanate groups in B resulting in urethane groups and n is from 0 to 50.

2. The vinylpyrrolidone polymer of claim 1, wherein vinylpyrrolidone polymer blocks carrying hydroxyl groups as functional end groups are linked by aliphatic dicarboxylic acids having a chain of from 0 to 10 carbon atoms between the two carbonyl groups, said hydroxyl groups and said carbonyl groups forming ester groups as connecting units.

3. The vinylpyrrolidone polymer of claim 1, wherein vinylpyrrolidone polymer blocks carrying hydroxyl groups as functional end groups are linked by aliphatic diisocyanates having a chain of from 2 to 10 carbon atoms between the two isocyanate groups, said hydroxyl groups and said isocyanate groups forming urethane groups as connecting units.

4. The vinylpyrrolidone polymer of claim 2, wherein the vinylpyrrolidone polymer block carrying hydroxyl groups is a copolymer of vinylpyrrolidone with small amounts of a comonomer.

5. A vinylpyrrolidone polymer as set forth in claim 1 wherein A is a homopolymer of vinylpyrrolidone.

6. A vinylpyrrolidone polymer as set forth in claim 1 wherein the average molecular weight of the polymer is from 1,000 to 1,000,000.

* * * * *